US005782869A

United States Patent [19]

Berdut

[11] Patent Number: 5,782,869

[45] Date of Patent: Jul. 21, 1998

[54] MULTI-TRAUMA THERAPEUTIC MACHINE

[76] Inventor: Elberto Berdut, Orquidea No. 98, Santa Maria, Guaynabo, Puerto Rico, 00926

[21] Appl. No.: 745,208

[22] Filed: Nov. 8, 1996

[51] Int. Cl.[6] .......... A61B 17/04

[52] U.S. Cl. .......... 606/242; 606/240; 601/24; 601/26; 5/609; 5/617; 5/618

[58] Field of Search .......... 606/240–242, 606/244, 245, 237; 601/24, 26, 49, 51, 53; 5/600, 609, 617, 618

[56] References Cited

U.S. PATENT DOCUMENTS

| | | | |
|---|---|---|---|
| 1,138,030 | 5/1915 | Weston | 606/242 |
| 1,375,652 | 4/1921 | Carlotti . | |
| 1,953,424 | 4/1934 | Miller . | |
| 2,976,868 | 3/1961 | Weissenberg | 606/245 |
| 3,404,679 | 10/1968 | Bevilacqua | 606/242 |
| 3,821,953 | 7/1974 | Mikan | 606/245 |
| 4,373,222 | 2/1983 | Wolfe et al. | 606/242 |
| 5,275,176 | 1/1994 | Chandler | 606/244 |

FOREIGN PATENT DOCUMENTS

| | | | |
|---|---|---|---|
| 2807256 | 8/1979 | Germany | 606/242 |

*Primary Examiner*—Gary Jackson
*Attorney, Agent, or Firm*—Ronald P. Kananen

[57] ABSTRACT

In order to therapeutically move and flex limbs of a person who has undergone severe trauma and who is in need of the assistance of a therapist, a table, which is slidably supported on a tiltable chassis, is connected with a drive mechanism which allows the stroke of reciprocative movement of the bed back and forth along the chassis, to be adjusted so that one or more pieces of supportive apparatus cyclically bend and straighten the arms and legs of a person on the bed in a manner which flexes the joints and muscles in the limbs and promotes blood circulation and other beneficial effects. The support structure, which supports the limbs of the patient, can be adjusted with respect to the chassis so that degree of limb flexure can be varied in accordance with individual/current needs.

13 Claims, 9 Drawing Sheets

MULTI-TRAUMA THERAPEUTIC MACHINE

BACKGROUND OF THE INVENTION

1. Field of the Invention

The present invention relates generally to a therapeutic machine. More specifically, the present invention relates to a motorized therapeutic machine which is designed to move limbs in a manner which facilitates circulation and muscular therapy necessary for the treatment of people who have suffered serious trauma or who have debilitating diseases/afflictions and the like.

2. Description of the Related Art

U.S. Pat. No. 1,375,652 and U.S. Pat. No. 1,953,424 both disclose a bed-like apparatus which is equipped with reciprocating pads that cyclically press against the body of a patient and mechanically induce the circulation of blood and manipulate the body without shock or injury. However, these arrangement have been unable to effectively treat the limbs and joints of the patient and thus have been of limited therapeutical use.

J-A-55-40544 published Mar. 22, 1980 discloses a floldable bed-like device which is intended for aesthetic applications and incorporates body pressing components in combination with supporting straps and localized pressure applying devices. However, this arrangement has not been able to simulate the effect produced by a therapist in connection with joint and muscle manipulation and therefore has met with only very limited success.

SUMMARY OF THE INVENTION

It is an object of the present invention to provide a therapeutic machine which induces joint and muscle movement and simulates the type of therapy that would be provided by a therapist per se.

It is a further object of the present invention to provide a therapeutic machine which is simple yet still highly adjustable.

Yet another object of the present invention is to provide a therapeutic machine which will exercise either legs or arms individually or both at the same time.

In brief, the above objects are achieved by an arrangement wherein a table, which is reciprocally mounted on a tiltable chassis, is connected with a drive mechanism which allows the stroke of reciprocative movement of the bed to be adjusted so that one or more pieces of supportive apparatus cyclically bend and straighten either or both of the arms and legs of a person on the bed, in a manner which manipulates the joints and muscles in the limbs and promotes blood circulation and other beneficial effects through the whole body. The support structure, which supports the limbs of the patient, can be adjusted with respect to the chassis so that degree of limb flexure can be varied in accordance with individual/current needs.

This machine was developed after years of scientific research with the cooperation of skillful engineers that were professionally advised by therapists and doctors specialized in muscular therapy and blood circulation related matters.

It was developed in order to offer a patient more flexibility and time in his or her therapy sessions without the need for the presence of an actual therapist.

The machine is adjustable and can be adapted to the patient's needs. For example, it can be adjusted for patients who have been in bed for a long period of time and need to improve the amount of blood circulation in order to maintain/improve their health/condition.

The first therapeutic exercises must consist of short easy movements in order to loosen and "warm-up" the joints and the muscles. As the patient adapts to this degree of muscle and joint flexure, the amount of movement can be increased until an optimum stage is reached.

Many different types of patients benefit from this machine. For example, people who have suffered cerebral vascular problems and who are totally or partially affected, people with chronic or partial muscular dystrophy, people having spinal problems due to accidents or sickness, and persons with arthritis or any illness that disables a patient from performing exercise on his or her own. Also, those patients who have had hip or knee surgery will benefit from the improved circulatory and muscular conditioning possible with the invention.

An embodiment of this machine is provided with an A.C. electric motor with a speed reduction gear that develops about 6 rpm. The speed reduction gear is connected to a 15 inch diameter disc. This disc is provided with a plurality of connection holes and is connected to a bed, which is slidably supported on a tiltable chassis, by way of a connecting rod or link. Once the motor is energized, linear reciprocal movement of the bed is produced.

A roller is connected by four beams (two sets of caliper arms) that work like scissors and which are arranged such that when reciprocative movement is induced, the roller is actuated and is driven up and down by an amount which varies in accordance with which connection hole in the disc the connecting rod or crank arm is connected and the amount of bed reciprocation that is accordingly produced. The backs of the patient's knees are supported on this roller while the patient's feet are supported on a hinged extension at the end of the bed. This extension is cammed to swing up and down in synchronization of the lifting and lowering of the patient's knees and thus assist in folding the legs about the knee.

Each reciprocal movement of the bed top lifts and lowers the knees creating movement in both the knees and hips. This movement can be adjusted from approximately zero up to a maximum angle needed by the patient undergoing the therapy. Each side of the machine is provided with a structure which allows the table on which a patient lies to be tilted with respect to the horizontal. The bed is cushioned such as with a quilted cushion and provided with adjustable belts for suitably securing the patient's body and hands in place. Each reciprocal movement of the machine produces a movement in the arms that bend the patient's elbows and raise the forearms until they are essentially at right angles to the trunk of the body. This movement works on the joints in the upper extremities promoting muscular movement and circulation.

More specifically, a first aspect of the invention resides in a therapeutic machine comprising: a chassis; a stand supporting the chassis; a bed slidably supported on the chassis so as to be slidably along an upper surface thereof; a motor supported on one of the chassis and the stand; drive means operatively connecting the motor and the bed for driving the bed to reciprocate back and forth along the chassis; and support means operatively connected with at least one of the chassis and the bed for supporting a limb of a person lying on the bed and for bending the limb in response to the reciprocative movement of the bed.

An important feature of the above arrangement resides in a pivotal extension member hingedly connected to one end of the bed; and cam means which includes a cam surface formed on the lower surface of the pivotal extension, and a cam follower operatively connected with the chassis, for raising and lowering the pivotal extension member in response to reciprocative movement of the bed.

A second aspect of the invention resides in a therapeutic machine comprising: a table which is reciprocatively supported atop of a chassis; drive means for driving the table to reciprocate back and forth along the chassis; and limb flexing means connected with one of the table and the chassis for at least one of cyclically lifting and lowering a knee of a patient prone on the table, and for cyclically moving an elbow of an arm of the patient inwardly and outward with respect to a trunk of the patient's body.

A third aspect of the invention resides in a therapeutic method comprising the steps of: placing a patient on a table which is reciprocatively disposed atop of a chassis; and supporting a limb of the patient using a structure which is pivotally supported on at least one of the table and the chassis, so that the limb is cyclically bent about a first joint about which upper and lower halves of the limb are articulated and cyclically moved about a joint which interconnects the limb with a trunk of the patient.

Yet another aspect of the invention resides in a therapeutic device comprising: a table which is reciprocatively disposed atop of a chassis and on which a patient is supported in a prone position; and means for supporting a limb of the patient which includes a structure pivotally supported on at least one of the table and the chassis, for cyclically bending the limb about a first joint about which upper and lower halves of the limb are articulated and cyclically moving the limb about a joint which interconnects the limb with a trunk of the patient.

BRIEF DESCRIPTION OF THE DRAWINGS

The various features, merits and advantages of the invention will become more clearly appreciated as a detailed description of the embodiment of the invention is given with reference to the appended drawings in which.

DETAILED DESCRIPTION OF THE PREFERRED EMBODIMENTS

Figure 1:
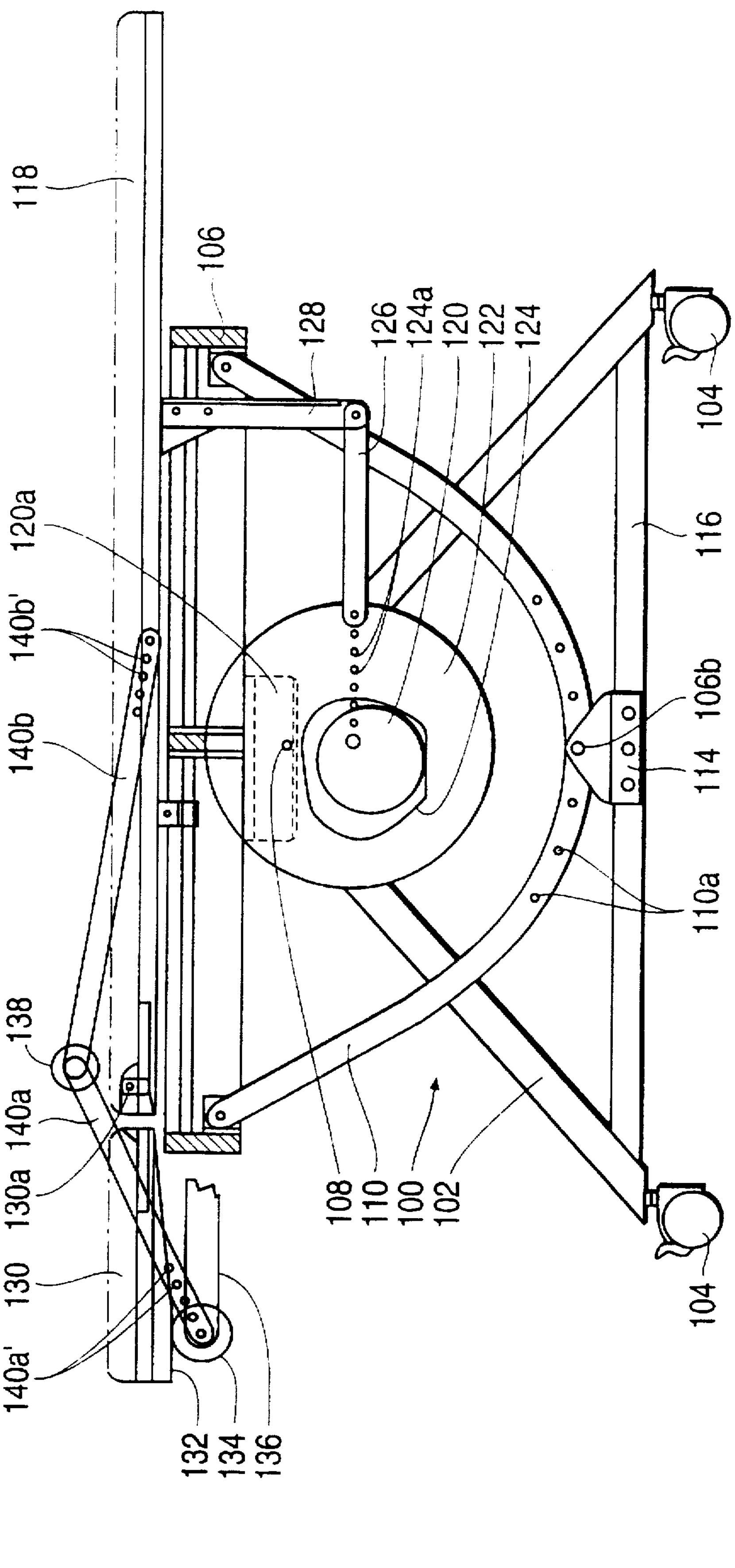
FIG. 1 is a schematic side elevation of an embodiment of the invention showing a leg flexing arrangement in an extended/low-lift condition wherein a foot support extension, hinged to the end of the bed, is held aligned with the bed portion of the apparatus.

The therapeutic machine according to the present invention includes a stand or base 100 which is made of tubular stainless steel. In this arrangement, the base 100 includes a pair of A-frames 102 having casters 104 at each corner. A chassis 106 is supported on the A-frames 102 so as to be pivotal about an axis shaft 108. A downwardly extending arcuately shaped stainless steel tilt control member 110 is connected to each side of the chassis 106. Each of these tilt control members 110 is formed with a plurality of pin holes **110*a* into which a locking pin 110*b* can be inserted to connect and lock the members 110 to brackets 114 which are rigid with reinforcing cross-braces 116 of each of the A-frames 102. By withdrawing the locking pins 110*b*, it is possible to selectively tilt the chassis 106** to any one of a number of predetermined angles with respect to the horizontal and then lock it in place.

A bed 118 is slidably supported on the chassis 106 through suitable roller bearings, rollers or the like. An electric motor 120 is supported on the chassis 106 by way of a motor mounting bracket **120*a* and is connected to a crank wheel 122 through a step down gearing 124 which reduces the rotational speed of the crank wheel to about 6 rpm in this embodiment. The crank wheel 124 is formed with a series of connection holes 124*a* to which an end of a connecting rod 126 can be selectively connected. As shown, this connecting rod or link 126 is pivotally connected to a downwardly depending bracket 128 which is rigidly connected to one side of the bed 118. With this arrangement, energization of the motor 120 induces the bed to slowly reciprocate back and forth along the top of the chassis 106** on which it is slidably supported.

One end of the bed 118 is provided with a pivotal extension member 130 which is adapted to support the feet of a patient lying on the main portion of the bed. This pivotal extension 130 is hinged to one end of the bed 118 by hinges **130*a*. The lower surface of the extension is provided with a cam surface 132 which engages a roller 134 that is supported between a pair of support bars 136 which are adjustably connected with the chassis 106. The combination of the cam surface 132 and the roller 134, which acts as a cam follower, produces a camming action which controls the angle at which the extension 130 is allowed to pivot downwardly as the bed 118 reciprocates back and forth. By changing the shape of the cam surface 132**, the timing and degree of the camming action can be varied.

Figure 2:
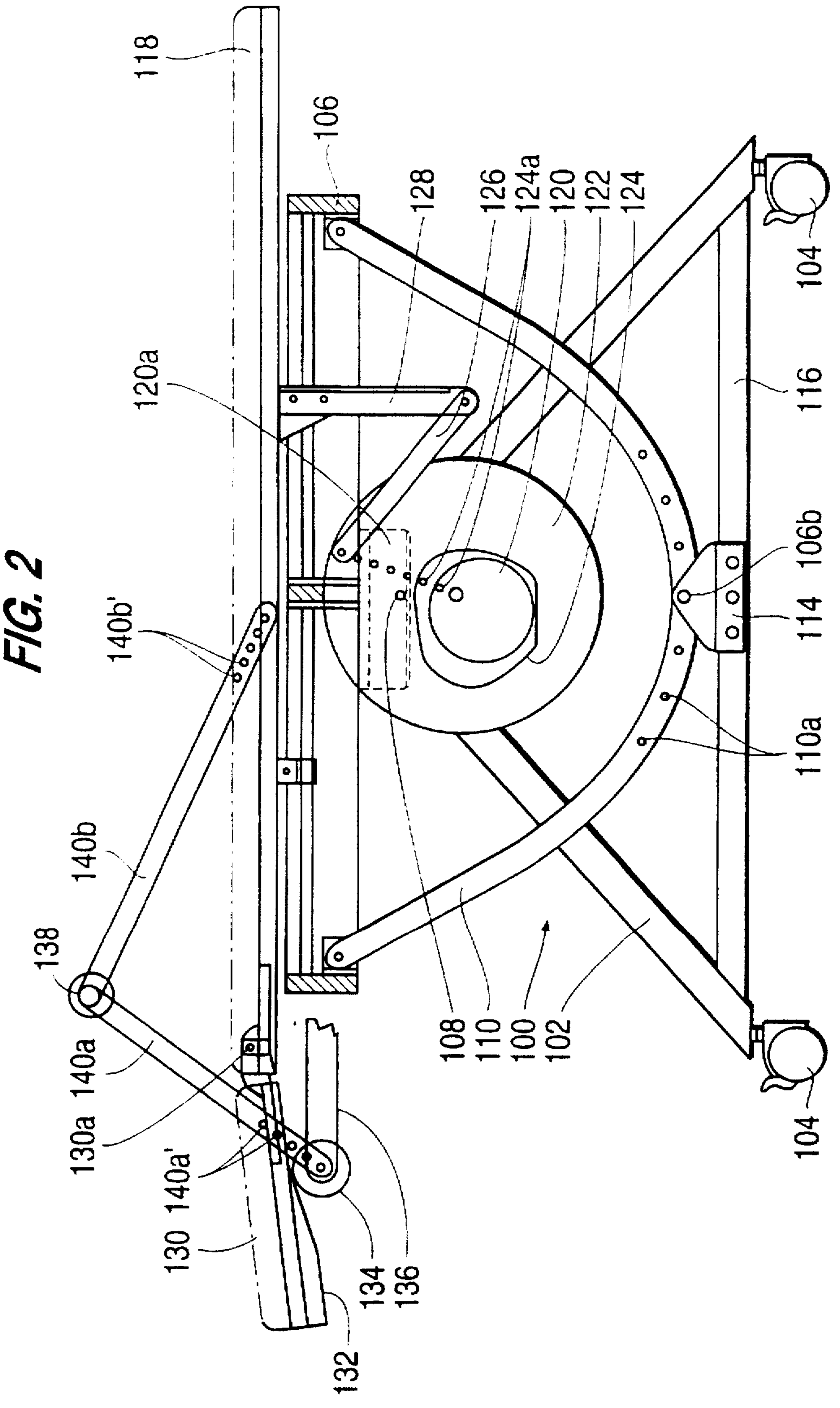
FIG. 2 is a schematic side elevation view showing the leg flexing arrangement in an partially contracted/intermediate-lift condition wherein a foot support extension is allowed to tilt down though a first small angle.
Figure 3:
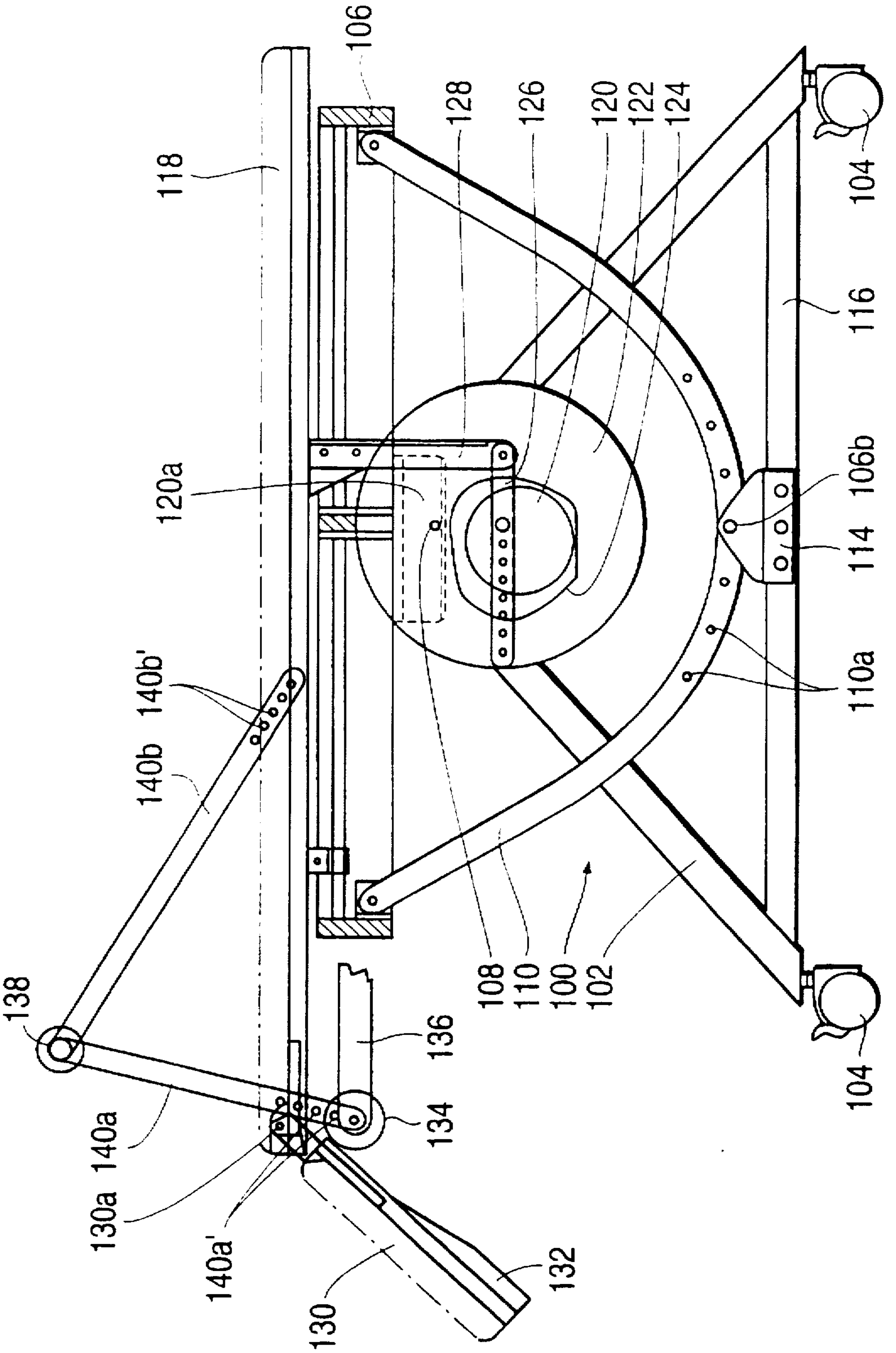
FIG. 3 is a schematic side elevation view showing the leg flexing arrangement in a fully contracted/high-lift condition, and a showing a foot rest extension in a fully tilted state.

A suitably padded leg lifting roller 138, which is intended to engage the back of the patient's knees, is connected with a pair of caliper arms **140*a*, 140*b* which are respectively connected to the support bars 136 and to the bed 118. With this arrangement, as the bed 118 reciprocates from the position shown in FIG. 1, to that shown in FIG. 3, the height of the leg lifting roller 138 shifts between a minimum and a maximum height with an intermediate lift being produced with the bed in the position shown in FIG. 2. At the same time, the foot supporting extension 130 is lowered from a position wherein it is aligned with the bed 118** (FIG. 1) through an intermediate angle (FIG. 2) to an angle of maximum tilt (FIG. 3). This tilting complements the lifting of the knees to comfortably increase the amount of bending the knee joints undergo.

Figure 4:
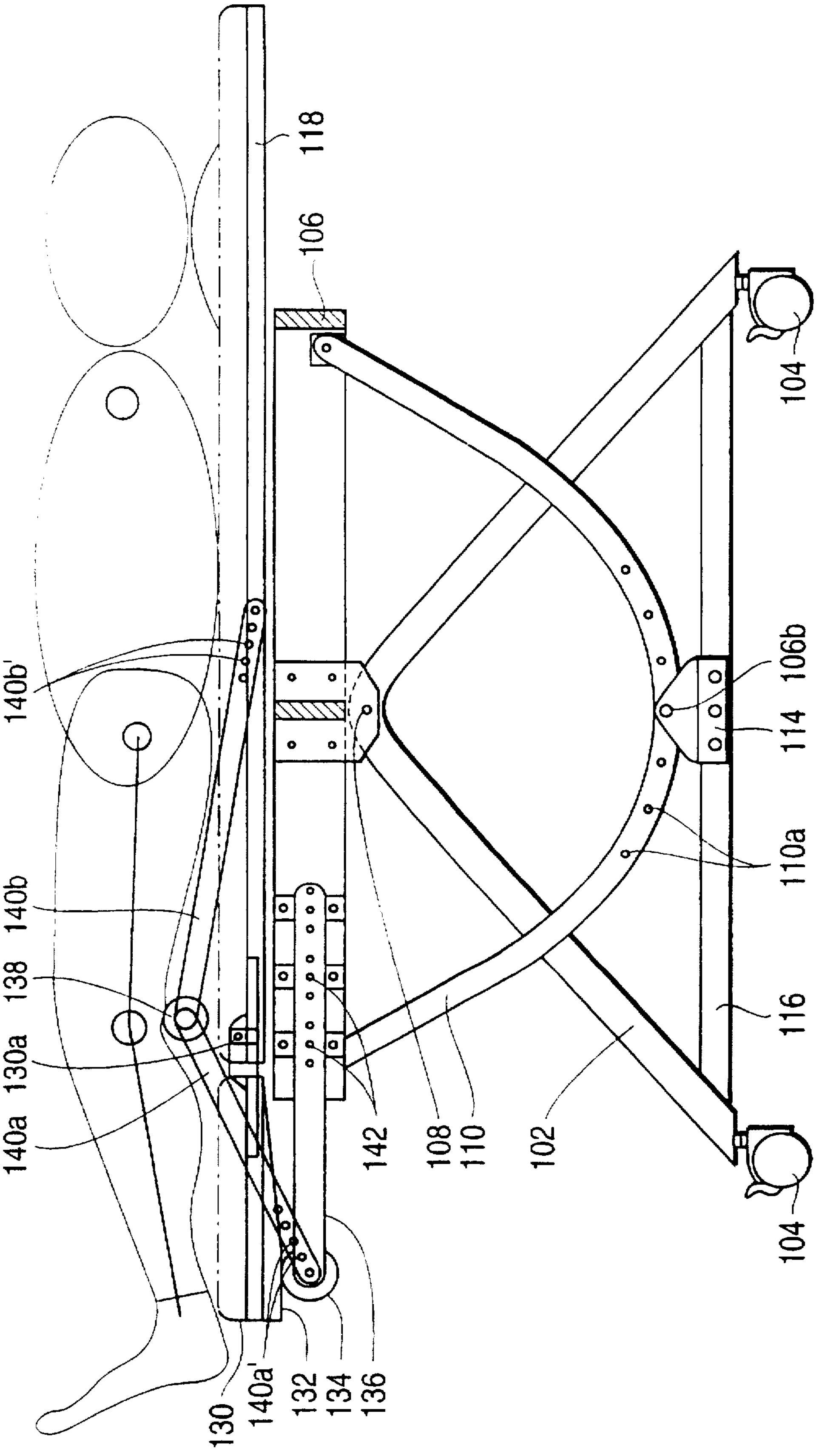
FIG. 4 is a view similar to FIG. 1 which omits illustration of the motorized arrangement which drives the table to reciprocate and which shows a patient lying on the bed portion of the machine with his or her legs in a fully extended minimally lifted/bent state.
Figure 5:
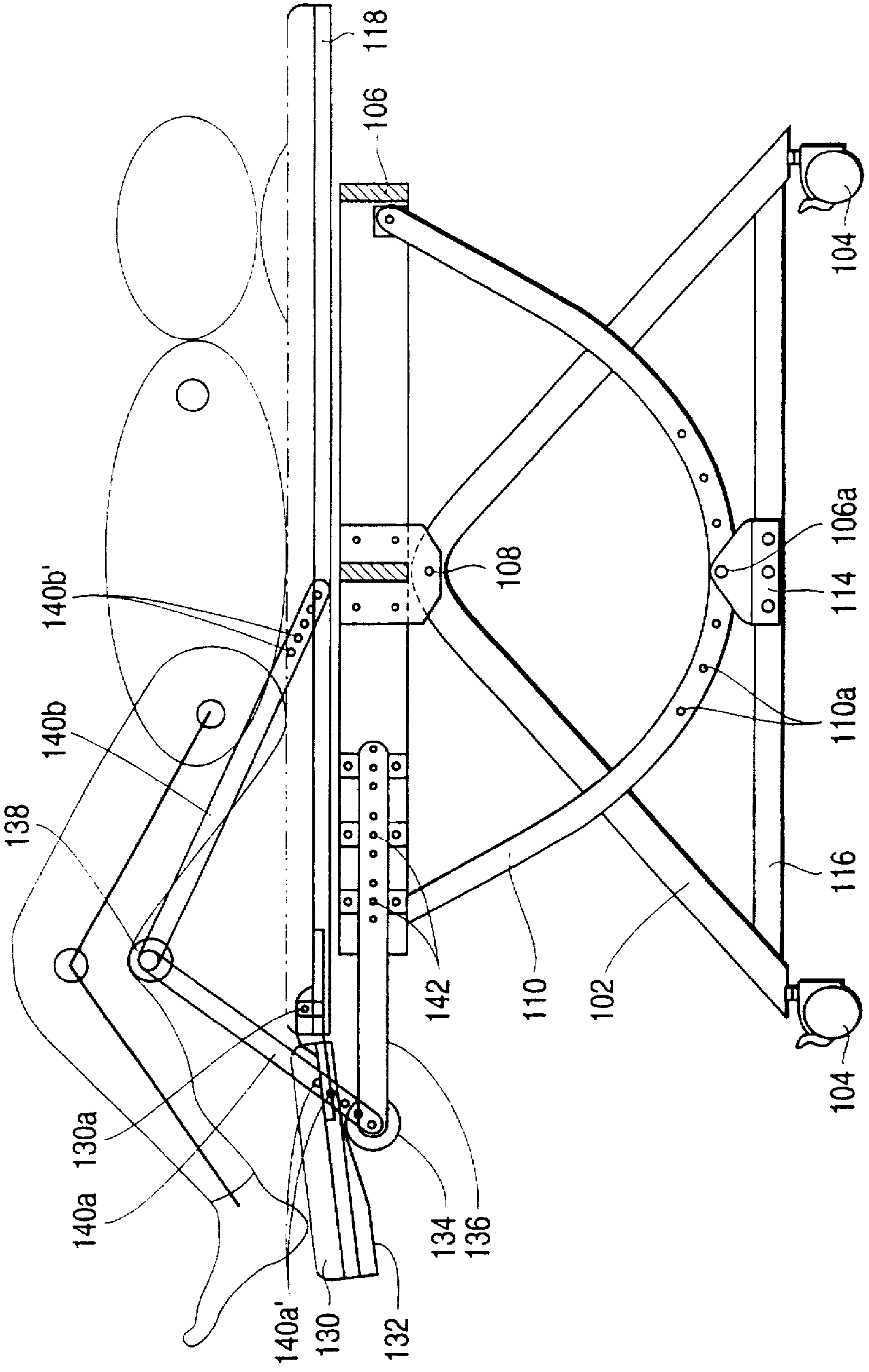
FIG. 5 is a view similar to FIG. 2 showing the patient's legs being flexed to an intermediate state.
Figure 6:
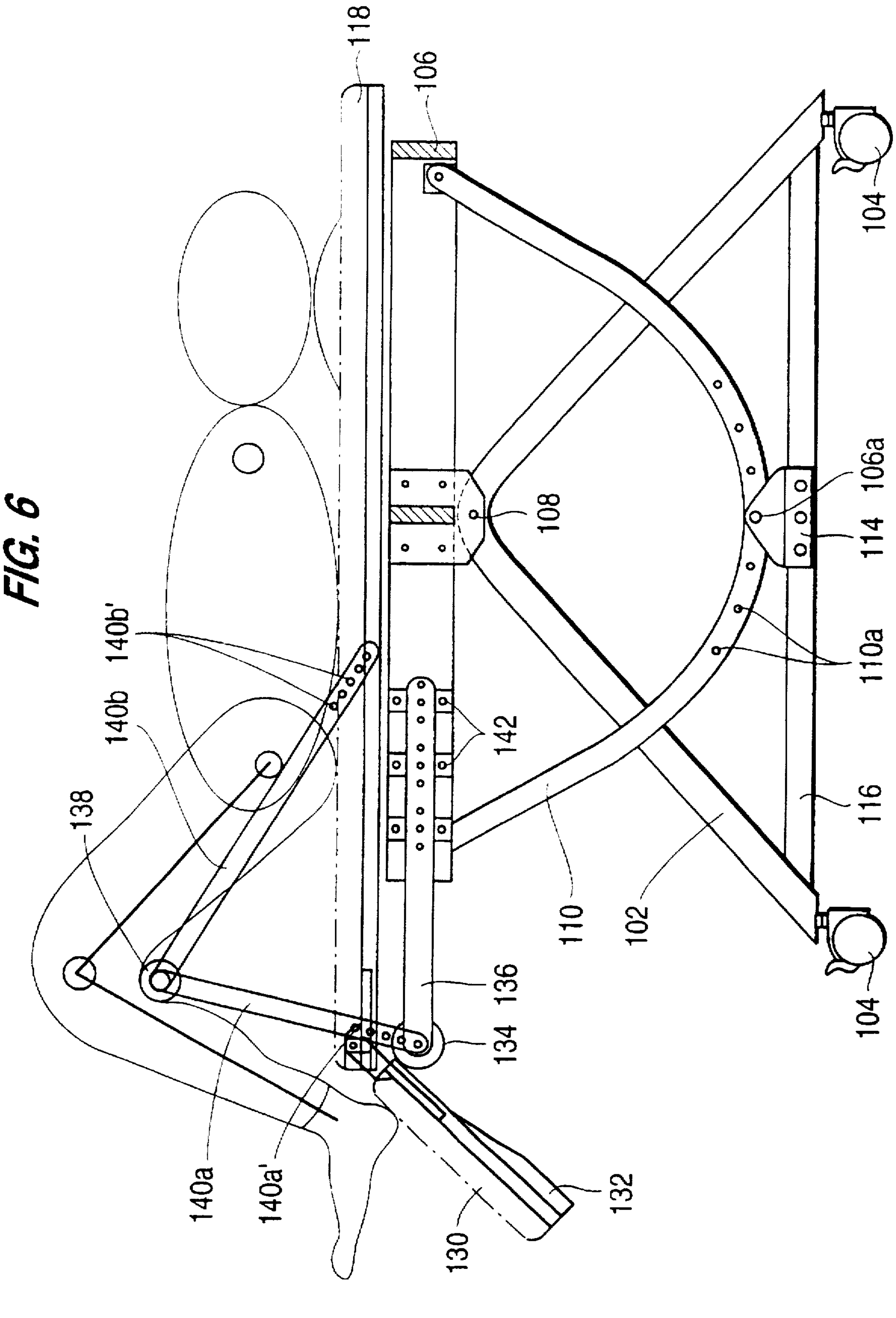
FIG. 6 is a view similar to FIG. 3 showing the patient's legs lifted to a state wherein maximum bending/flexure occurs.
Figure 7:
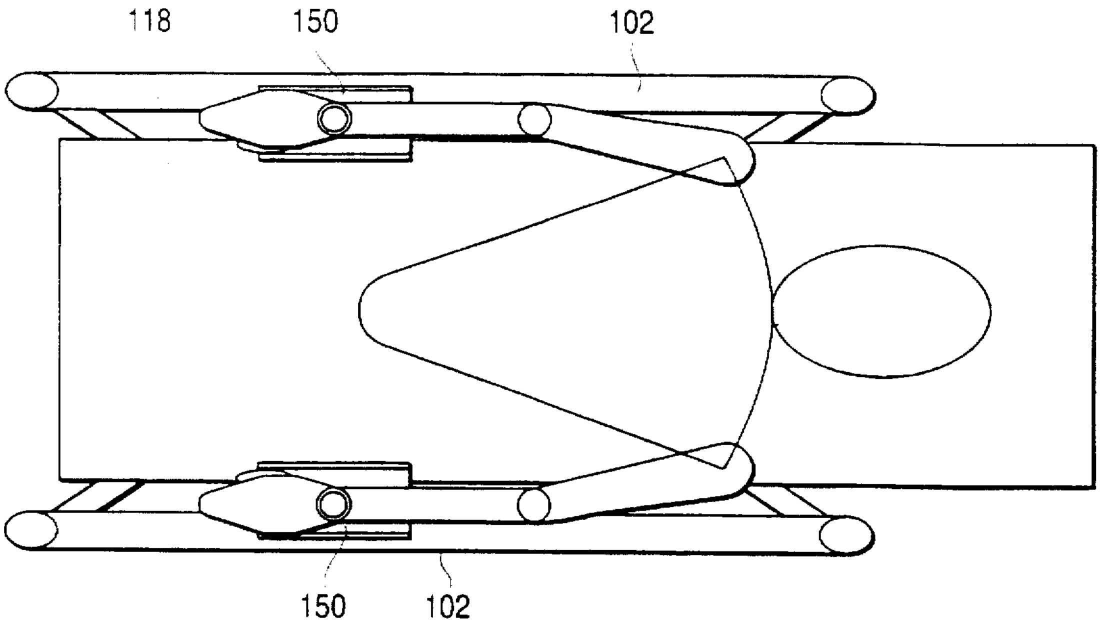
FIG. 7 is a plan view showing a structure which is directed to inducing therapeutic movement in a patient's arms and which is such that the patient's arms are essentially straight and in a state of a minimum flexure.
Figure 8:
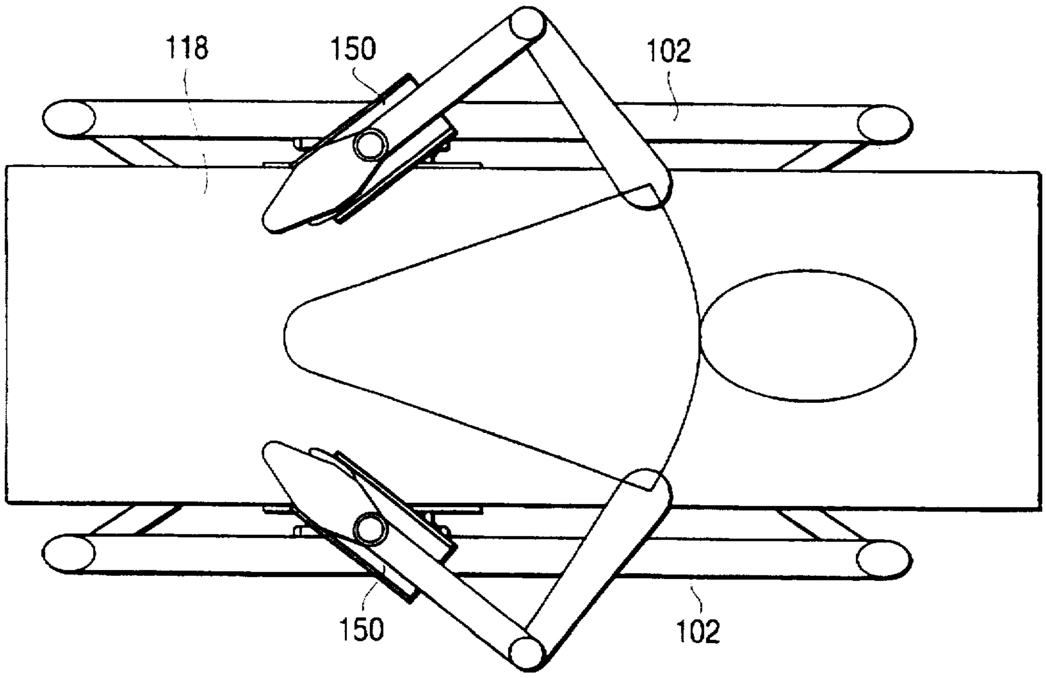
FIG. 8 is a plan view similar to that shown in FIG. 7 but showing the table portion moved to a position wherein the patient's arms are partially flexed.
Figure 9:
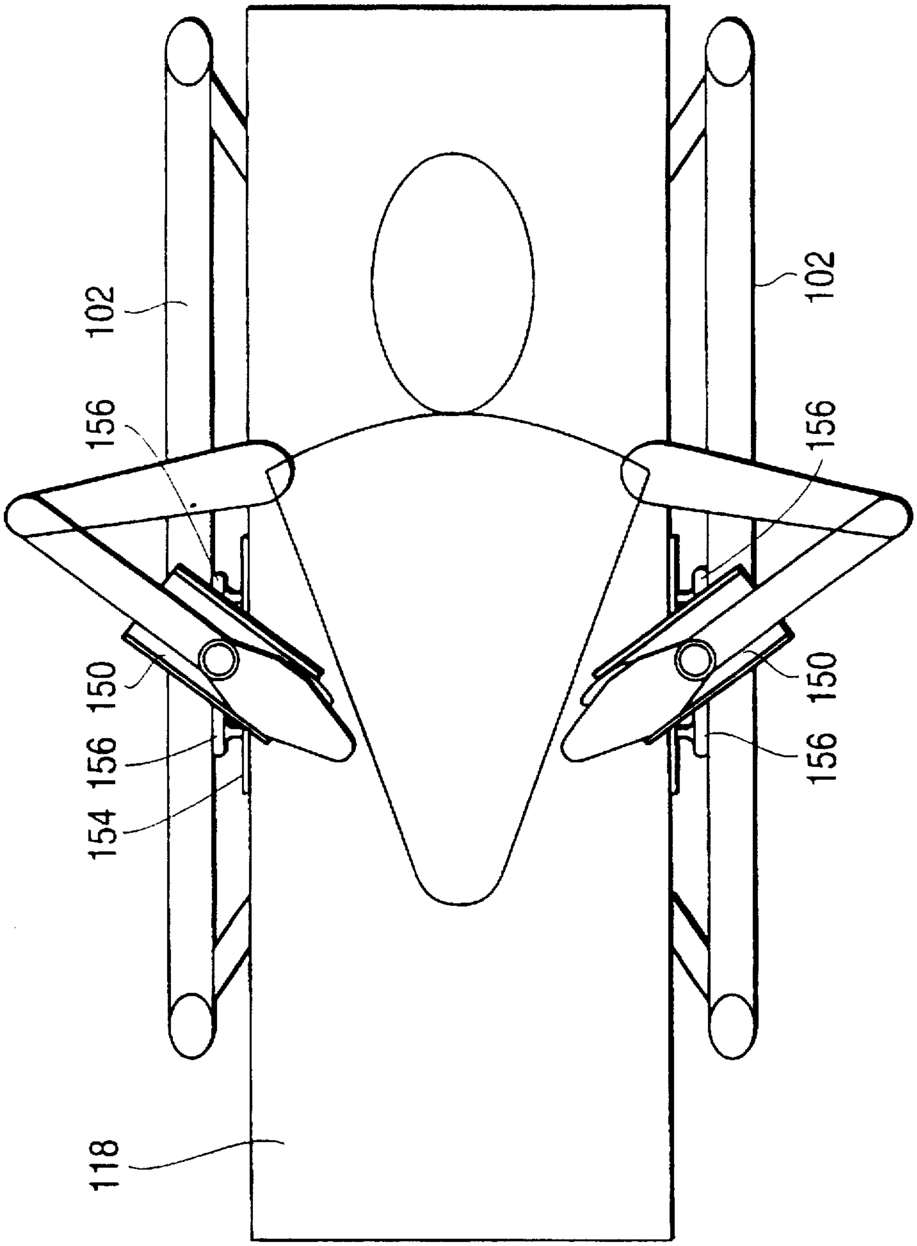
FIG. 9 is a plan view similar to those shown in FIGS. 7 and 8 showing the table in a position wherein the patient's arms are fully flexed.

The effect of this machine on a patient, who is lying on the bed, is illustrated in FIGS. 4 to 6. As shown in these figures, the legs of the patient are lifted in a manner which causes the knees to bend and for the upper legs to rotate about the hip joints. As the knees are lifted, the heels of the patient are allowed to lower due to the change in attitude of the extension induced by the camming action of the roller 134 and the cam surface 132. The amount of knee bending is accordingly increased.

The action of the knee lift roller 138 and the camming action provided by the roller, are variable. As is clear from FIGS. 4 to 6, the support bars 136 are connected to the chassis by way of three connection pins 142 and are provided with additional connection holes which allow the degree of projection of the bars 136 to be adjusted. That is to say, by removing the connection pins 142 and moving the support bars 136 to new positions and then reconnecting the connection pins 142, the distance between the chassis 106 and the cam roller 134 can be adjusted in a manner which varies the timing and tilting of the foot support extension 130. This embodiment is by no means limited to this type of connection and the use of telescopically arranged tubular members with a single lock screw is quite within the scope of the invention.

The ends of the caliper arms 140*a*, 140*b* are also provided with a plurality of spaced connection holes 140*a*', 140*b*' so that connection pins (no numeral), which respectively connect the ends of the arms 140*a*, 140*b* to the support bars 136 and bed 118, can be removed and the height to which the knee lift roller 138 is raised in response to each stroke of the bed, can be adjusted.

It will be noted that, although the above description makes reference to locking pins and connection pins, these locking elements can be constituted by any convenient form of connection device such as a bolt having a knurled head, T-bar grip or the like, and may be provided with a shaped head which facilitates manipulation and adjustment.

FIGS. 7 to 10 show an arrangement which allows therapeutic movement of the patient's arms to be induced in response to the reciprocative movement of the bed. This arrangement is relatively simple and features channel-like arm supports 150 onto which portions of the lower arm can be placed and strapped or otherwise gently restrained. These supports 150 are arranged to be supported by shafts 152 (see FIG. 10B) which can rotate or pivot about axes which, in this embodiment, extend normally with respect to the plane of the bed. Alternatively, the supports can be pivotally supported on the tops of the shafts.

Figures 10A, 10B:
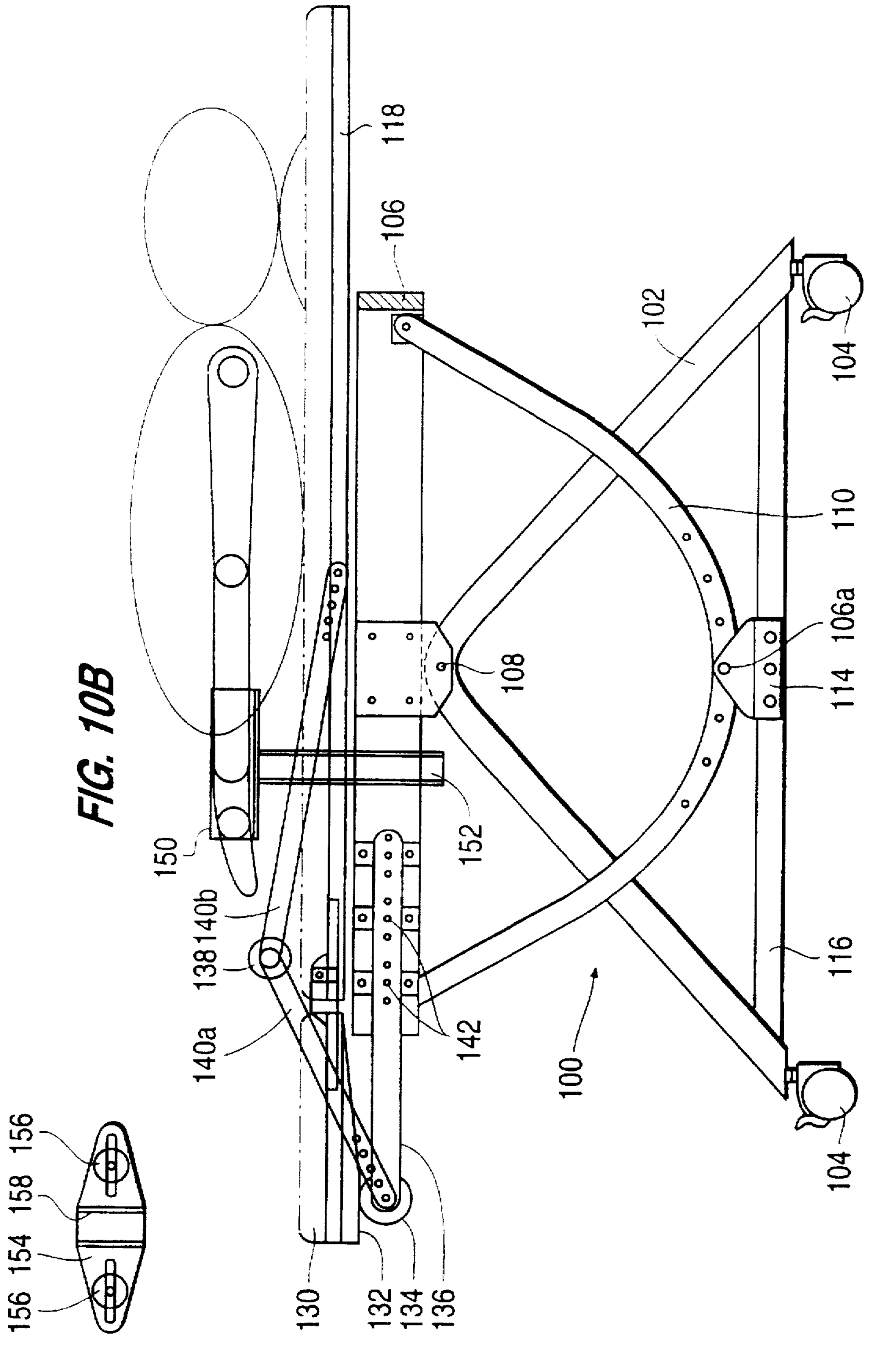
FIGS. 10A and 10B are side elevations showing a structure which allows the positions of the arm support arrangements to be adjusted.

FIGS. 10A and 10B shown the manner in which the arm supports 150 can be adjustably connected to the side of the chassis 106. A support bracket 154 arrangement of the nature depicted in FIG. 10A is adapted to be connected to the side of the chassis by way of suitable adjust screws 156 or the like. With this arrangement, by loosening the screws 156, it is possible to slide the support bracket 154 laterally along the side of the chassis 106 to a position wherein the amount of arm flexure is either increased or decreased depending of the therapeutic effect that is desired. The height of the arm supports 150 with respect to the top of the bed 118 152 is also adjustable. In this case, the shafts on which the arms supports are supported are formed with a thread and are threadedly received in a tapped bore 158 formed in the support bracket 154. Simply by spinning the arm supports 150, the height of the supports 150 with respect to the bed 118 can be adjusted, the threaded connection also allowing the desired rotation of the arm supports as the bed reciprocates back and forth.

It will be understood that the invention has been described with reference to only one embodiment and that many and various modifications are possible without departing from the scope of the invention which is only limited by the appended claims. For example, while it is possible to use the leg and arm flexing arrangements at the same time, it is possible to use only one at a time.

What is claimed is:

1. A therapeutic machine comprising:

a chassis;

a stand tiltably supporting said chassis, so as to tilt the chassis at different angles relative to a horizontal plane;

a bed slidably supported on said chassis so as to be slidably along an upper surface thereof;

a motor supported on one of said chassis and said stand;

drive means operatively connecting said motor and said bed for driving the bed to reciprocate back and forth along said chassis; and support means operatively connected with at least one of said chassis and said bed for supporting a limb of a person lying on said bed and for bending the limb in response to the reciprocative movement of said bed.

2. A therapeutic machine as set forth in claim 1, further comprising:

a pivotal extension member hingedly connected to said bed; and cam means comprising a cam surface formed on the lower surface of said pivotal extension and a cam follower operatively connected with said chassis for raising and lowering the pivotal extension member in response to reciprocative movement of said bed.

3. A therapeutic machine as set forth in claim 2, wherein said cam follower comprises a roller which is supported on support bars which project out from one end of the chassis, the support bars being adjustably connected to said chassis so that a distance between said roller and said chassis is variable and the timing with which the cam means pivots said pivotal extension member is adjustable.

4. A therapeutic machine as set forth in claim 1, wherein said support means comprises a knee support roller which is connected to said chassis and said bed by a pair of caliper arms, said caliper arms being connected with said chassis and said bed so that movement of bed relative to said chassis changes the angle between the caliper arms and changes the displacement of said knee support roller with respect to a plane of the bed.

5. A therapeutic machine as set forth in claim 4, further comprising adjustment means for adjusting the amount by which said limb is bent during reciprocation of said bed.

6. A therapeutic machine as set forth in claim 5, wherein said adjustment means comprises means for adjusting the length of said caliper arms.

7. A therapeutic machine as set forth in claim 1, wherein said support means comprises arm supports which are supported on said chassis so as to be pivotal about an axis which is essentially normal to the direction in which said bed is reciprocative.

8. A therapeutic machine as set forth in claim 1, wherein said drive means includes a crank arrangement including:

a disc;

a step down gear between the motor and said disc; and a link pivotally connected to said disc at a first end and pivotally connected to said bed at a second end thereof.

9. A therapeutic machine as set forth in claim 8, wherein said disc is provided with a plurality of connection points which allow said link to be selectively connected to said disc at different radii from the axis of rotation of said disc and therefore adjust a length of a stroke of said bed along said chassis.

10. A therapeutic machine as set forth in claim 1, further comprising: pivot means interconnecting said chassis and said stand for allowing said chassis to be selectively tilted with respect to said stand.

11. A therapeutic machine comprising:

a table which is reciprocatively supported atop of a tiltable chassis;

drive means for driving the table to reciprocate back and forth along said chassis; and limb flexing means connected with one of said table and the chassis for at least one of cyclically lifting and lowering a knee of a patient prone on said table and for cyclically moving an elbow of an arm of the patient inwardly and outward with respect to a trunk of the patient's body.

12. A therapeutic method comprising the steps of:

placing a patient on a table which is reciprocatively disposed atop of a tiltable chassis; and supporting a limb of the patient using a structure which is pivotally supported on at least one of the table and the chassis, so that the limb is cyclically bent about a first joint about which upper and lower halves of the limb are articulated and cyclically moved about a joint which interconnects the limb with a trunk of the patient.

13. A therapeutic device comprising:

a table, for supporting a patient, which is reciprocatively disposed atop of a tiltable chassis and on which the patient is supported in a prone position; and means for supporting a limb of the patient which includes a structure pivotally supported on at least one of the table and the chassis, for cyclically bending the limb about a first joint about which upper and lower halves of the limb are articulated and cyclically moving the limb about a joint which interconnects the limb with a trunk of the patient.

* * * * *